United States Patent
Millet et al.

(10) Patent No.: US 10,376,450 B2
(45) Date of Patent: Aug. 13, 2019

(54) ANHYDROUS DEODORANT COMPOSITION MADE FROM BICARBONATE

(71) Applicant: LABORATOIRES M&L, Manosque (FR)

(72) Inventors: Magali Millet, Les Mees (FR); Florian Salles, Manosque (FR)

(73) Assignee: LABORATOIRES M&L, Manosque (FR)

( * ) Notice: Subject to any disclaimer, the term of this patent is extended or adjusted under 35 U.S.C. 154(b) by 0 days.

(21) Appl. No.: 15/575,590

(22) PCT Filed: May 10, 2016

(86) PCT No.: PCT/FR2016/051095
§ 371 (c)(1),
(2) Date: Nov. 20, 2017

(87) PCT Pub. No.: WO2016/185113
PCT Pub. Date: Nov. 24, 2016

(65) Prior Publication Data
US 2018/0168954 A1    Jun. 21, 2018

(30) Foreign Application Priority Data
May 21, 2015   (FR) ..................... 15 54552

(51) Int. Cl.
| | |
|---|---|
| *A61K 8/19* | (2006.01) |
| *A61K 8/25* | (2006.01) |
| *A61K 8/34* | (2006.01) |
| *A61K 8/39* | (2006.01) |
| *A61Q 15/00* | (2006.01) |
| *A61K 8/73* | (2006.01) |
| *A61K 8/92* | (2006.01) |

(52) U.S. Cl.
CPC .............. *A61K 8/19* (2013.01); *A61K 8/25* (2013.01); *A61K 8/345* (2013.01); *A61K 8/39* (2013.01); *A61K 8/732* (2013.01); *A61K 8/922* (2013.01); *A61Q 15/00* (2013.01); *A61K 2800/31* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,376,363 A | 12/1994 | Benfatto et al. | |
| 2003/0157044 A1* | 8/2003 | Tomczak | A61K 8/044 424/65 |
| 2008/0014160 A1* | 1/2008 | Faivre | A61K 8/042 424/65 |

FOREIGN PATENT DOCUMENTS

CA    2 808 807    9/2014

OTHER PUBLICATIONS

Written Opinion in International Application No. PCT/FR2016/051095, dated Jul. 18, 2016, pp. 1-6.

* cited by examiner

*Primary Examiner* — Johann R Richter
*Assistant Examiner* — Danielle Sullivan
(74) *Attorney, Agent, or Firm* — Saliwanchik, Lloyd & Eisenschenk

(57) ABSTRACT

The present invention relates to an anhydrous cosmetic composition made from bicarbonate salt, and the cosmetic use of same as a deodorant. The invention also relates to a deodorant product containing said composition.

9 Claims, No Drawings

ANHYDROUS DEODORANT COMPOSITION MADE FROM BICARBONATE

CROSS-REFERENCE TO RELATED APPLICATION

This application is the U.S. national stage application of International Patent Application No. PCT/FR2016/051095, filed May 10, 2016.

SUBJECT OF THE INVENTION

The present invention relates to an anhydrous cosmetic composition based on bicarbonate salt, and also to the cosmetic use thereof as a deodorant. It also relates to a deodorant product containing this composition.

BACKGROUND OF THE INVENTION

Deodorants and antiperspirants have become hygiene products that are as indispensable as shampoos and toothpastes. Although the former act on perspiration odors either by camouflaging them or by targeting the bacteria that feed on apocrine sweat, or else by absorbing the perspiration, the latter regulate the amount of sweat emitted. The safety of the aluminum salts used as antiperspirant agents has been called into question in recent years, which has resulted in consumers turning to products that contain natural deodorant agents such as talc and/or certain plants in dried form or in the form of essential oils. However, the effectiveness of these products is still not optimal.

Sodium bicarbonate forms a recognized natural deodorant active agent. At the doses considered to be effective, its formulation is on the other hand complicated by its incompatibility with many raw materials, in particular when it must be formulated in solid or semi-solid anhydrous compositions having good cosmetic properties.

SUMMARY OF THE INVENTION

After much research, the applicant has developed a composition in which effective amounts of bicarbonate salt may be combined with a large amount of oils without adversely affecting the stability of the composition. It is thus possible to formulate anhydrous deodorants in cream form or in the form of sticks of soft texture, based on ingredients of natural origin. These compositions have proved easy to apply, effective against perspiration odors and capable of depositing a soft, non-greasy and non-tacky film on the skin.

One subject of the invention is thus an anhydrous cosmetic composition containing:
(a) from 1% to 20% by weight of at least one bicarbonate salt,
(b) from 20% to 50% by weight of at least one oil,
(c) at least one fatty-phase structuring agent,
(d) glycerol, and
(e) at least one polyglycerol ester of a fatty acid containing from 12 to 30 carbon atoms.

Another subject is the cosmetic use of this composition for treating human body odors, in particular axillary odors.

Lastly it relates to a deodorant product in the form of a tube, pot or any other packaging, in particular of oblong shape, suitable for dispensing a semi-solid composition, containing the composition according to the invention in cream form, or in a packaging form suitable for dispensing a stick, containing the composition according to the invention in stick form.

DETAILED DESCRIPTION

The composition according to the invention is an anhydrous composition, in the sense that it contains less than 5% by weight of water, advantageously less than 1% by weight of water, which may be introduced solely by its constituent ingredients. Preferably it contains no water.

It comprises a bicarbonate salt as deodorant agent. This may represent from 1% to 20% by weight, and preferably from 5% to 15% by weight, relative to the total weight of the composition. As bicarbonate salts, mention may be made of sodium, potassium, magnesium and ammonium salts, the sodium salt being preferred for use in this invention. According to one embodiment, the composition does not contain aluminum salts. On the other hand, it may however contain at least one additional deodorant active agent chosen from: bacteriostatic or bactericidal agents, such as chlorhexidine and salts thereof; triclosan; triclocarban; farnesol; essential oils of plant origin, chosen for example from oregano, palmarosa, peppermint, lavender, lemon and tea tree essential oils; plant extracts such as grapefruit seed extracts; zinc salts such as zinc gluconate, pidolate and ricinoleate; and mixtures thereof.

As indicated previously, it was observed that the composition according to the invention was stable in the presence of bicarbonate, even though it contains large amounts of oil, namely from 20% to 50% by weight, and in particular from 25% to 40% by weight, of one or more oils, relative to the total weight of the composition. Within the meaning of the present invention, an "oil" is understood to mean a compound that is liquid at room temperature (25° C.) and atmospheric pressure (105 Pa) which, when it is introduced in a proportion of at least 1% by weight into water at 25° C., is not at all soluble in water, or is soluble up to less than 10% by weight, relative to the weight of oil introduced into the water. The oils may be volatile or nonvolatile. A "nonvolatile oil" is understood in this description to mean an oil that remains on the skin at 25° C. and atmospheric pressure for at least one hour, in the absence of rubbing, and/or that has a vapor pressure of less than 0.001 mmHg under these conditions. The oils included in the composition according to the invention may or may not be volatile; advantageously they are nonvolatile. As a variant, it may be a mixture of nonvolatile oils (in the majority by weight) and volatile oils (in the minority by weight). Examples of volatile oils are in particular C11 to C14 linear alkanes. Moreover, the nonvolatile oils are preferably chosen from hydrocarbon-based oils, that is to say that they contain exclusively carbon atoms, hydrogen atoms and optionally oxygen atoms.

Examples of nonvolatile oils include:
  esters of acids and of monoalcohols chosen from:
    monoesters and polyesters of C2-C10 (preferably C6-C10) saturated linear acids and of C10-C18 (preferably C10-C14) saturated linear monoalcohols, monoesters and polyesters of C10-C20 saturated linear acids and of C3-C20 (preferably C3-C10) branched or unsaturated monoalcohols; monoesters and polyesters of C5-C20 branched or unsaturated acids and of C5-C20 branched or unsaturated monoalcohols; monoesters and polyesters of C5-C20 branched or unsaturated acids and of C2-C4 linear monoalcohols;
  triglycerides of C6-C12 fatty acids, such as triglycerides of caprylic and capric acids and triheptanoin;
  C10-C20 branched and/or unsaturated fatty acids (such as linoleic, lauric and myristic acids);
  C10-C20 branched and/or unsaturated fatty alcohols (such as octyldodecanol and oleyl alcohol);

hydrocarbons such as plant squalane extracted from olive oil;

dialkyl carbonates, such as dicaprylyl carbonate and diethylhexyl carbonate;

dialkyl ethers such as dicaprylyl ether; and mixtures thereof.

Mention may also be made of the plant oils that contain one or more of the aforementioned constituents.

As esters of acids and of monoalcohols which form the preferred class of nonvolatile oils according to the invention, mention may in particular be made of monoesters such as the mixture of coco caprate and caprylate, ethyl macadamiate, shea butter ethyl ester, isostearyl isostearate, isononyl isononanoate, ethylhexyl isononanoate, hexyl neopentanoate, ethylhexyl neopentanoate, isodecyl neopentanoate, isostearyl neopentanoate, isodecyl neopentanoate, isopropyl myristate, octyldodecyl myristate, isopropyl palmitate, ethylhexyl palmitate, hexyl laurate, isoamyl laurate, cetostearyl nonanoate, propylheptyl caprylate and mixtures thereof. Other esters that can be used are the diesters of acids and of monoalcohols such as diisopropyl adipate, diethylhexyl adipate, diisopropyl sebacate and diisoamyl sebacate.

Examples of plant oils are in particular wheatgerm oil, sunflower oil, argon oil, hibiscus oil, coriander oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, lavender oil, borage oil, millet oil, barley oil, *quinoa* oil, rye oil, safflower oil, candlenut oil, passion flower oil, musk rose oil or *camellia* oil.

In order to obtain a stable composition having good cosmetic properties, the composition according to the invention additionally contains a combination of at least one fatty-phase structuring agent with glycerol and at least one polyglycerol ester of a fatty alcohol containing from 12 to 30 carbon atoms.

A "fatty-phase structuring agent" is understood to mean a compound capable of thickening the oils contained in the composition, chosen in particular from waxes, fatty-phase gelling agents and pasty fatty substances, and also mixtures thereof.

The term "wax" denotes, within the context of this description, a fatty substance that is solid at 25° C., with a reversible solid/liquid change of state, having a melting point generally between 30° C. and 160° C., preferably between 50° C. and 90° C., as measured by DSC. Examples of waxes are in particular waxes of animal or plant origin, such as beeswax, Chinese insect wax, candelilla wax, carnauba wax or acacia wax; hydrogenated plant oils that are optionally modified by isostearic acid, in particular hydrogenated rapeseed, soybean, sunflower, jojoba, coconut and castor oils; esters of C14-C30 saturated linear fatty acids and of C16-C36 saturated linear fatty alcohols; C10-C30 linear and saturated acids; C8-C30 linear and saturated alcohols; and mixtures thereof. These waxes may be in micronized form, that is to say in the form of a powder, the particles of which have a number-average size of less than or equal to 50 µm, and in particular ranging from 0.5 to 50 µm, preferably ranging from 1 to 30 µm, or even ranging from 3 to 20 µm, where the "number-average size" corresponds to the dimension given by the statistical particle size distribution to half of the population, referred to as D50.

The expression "fatty-phase gelling agents" refers to the compounds that modify the rheology of the fatty phase by forming a three-dimensional network. As compounds of this type, mention may especially be made of hydrophobic modified clays (in particular bentonites and hectorites), in particular that are modified by di stearyldimethylammonium chloride; hydrophobic modified fumed silicas; dextrin palmitate and myristate; polyamides, olefin(s)/styrene copolymers, poly(alkyl acrylates); glycerides of $C_{16}$-$C_{26}$ (preferably linear and saturated) fatty acids such as the compound Nomcort® HKG; cellulose derivatives and mixtures containing same; and mixtures thereof. Certain hydrogenated plant oils may also be considered to be fatty-phase gelling agents.

Finally, the pasty fatty substances that can be used as fatty-phase structuring agents are defined as fatty substances with a reversible solid/liquid change of state, having in the solid state an anisotropic crystalline organization and comprising at a temperature of 23° C. a liquid fraction and a solid fraction. Use is preferably made of plant butters. Shea, cocoa and mango butters constitute examples of such pasty fatty substances.

According to one preferred embodiment, the fatty-phase structuring agent included in the composition according to the invention consists of at least one ingredient chosen from waxes of animal origin, waxes of plant origin, fatty-phase gelling agents and mixtures thereof, optionally combined with at least one plant butter. More preferentially still, the fatty-phase structuring agent consists of a combination of at least one animal and/or plant wax with at least one fatty-phase gelling agent.

These fatty-phase structuring agents may represent from 5% to 40%, and preferably from 15% to 30% of the total weight of the composition.

Another constituent of the composition according to the invention, contributing to its stability, is glycerol. This may represent from 1% to 15% and preferably from 3% to 10% of the weight of the composition.

The composition according to the invention also contains at least one polyglycerol ester of a fatty acid containing from 12 to 30, preferably from 18 to 22 carbon atoms. The fatty acid may be chosen from saturated linear acids, saturated branched acids, monounsaturated linear acids and mixtures thereof. These acids may optionally be monohydroxylated or polyhydroxylated. Examples of such compounds are in particular stearic, isostearic, capric, arachidic, behenic, hydroxypalmitic, hydroxystearic, oleic and erucic acids. The polyglycerol may be obtained by condensation of two to six glycerol units. It is preferably polyglycerol-3 or -4. The polyglycerol may be partially or completely esterified in order to obtain the ester used in the present invention. It may particular be the product of the esterification of a wax using polyglycerol. A product of this type is commercially available from GATTEFOSSE under the trade name Acticire®.

This ester may represent from 0.1% to 5% and preferably from 0.5% to 3% of the total weight of the composition.

The composition according to the invention additionally advantageously contains one or more pulverulent fillers, which are suitable for absorbing moisture and sweat and which are generally in the form of porous or hollow microparticles, preferably porous microparticles. These microparticles are in principle substantially spherical. These fillers may in particular be chosen from:

organic fillers such as: powders of polysaccharides and in particular of native starch, of modified starch and cellulose; powders of acrylic polymers such as poly (methyl methacrylate), polyamides or polyolefins; powders of dried algae such as *Corallina officinalis;* inorganic fillers such as silica, clays, perlite and talc;

and mixtures thereof.

The starches are preferably chosen from corn starch, rice starch, tapioca starch or wheat starch. The modified starches constitute preferred organic fillers for use in this invention. Examples of modified starches are the optionally pre-gelatinized and/or oxidized starches, that are esterified by an alkenylsuccinic anhydride, in particular by octenylsuccinic or dodecylsuccinic anhydride, optionally in the presence of calcium chloride, and also etherified starches, in particular hydroxypropylated or carboxymethylated starches, and cationic starches, in particular quaternized starches. Mention may also be made of the starch crosslinked by sodium trimetaphosphate. As inorganic filler, use is preferably made of silica.

These fillers may represent from 10% to 30% by weight, preferably from 15% to 30% by weight, relative to the total weight of the composition.

It may additionally comprise additives chosen in particular from fragrances, antioxidants such as tocopherol, dyes, preservatives and mixtures thereof.

It is preferred for the composition according to the invention to contain an amount of at least 90% by weight of ingredients of plant origin, as determined according to the ASTM D7026 standard.

The composition described above may be used as a deodorant product, which may be in cream form (advantageously having the texture of a balm) or stick form advantageously having a soft texture.

EXAMPLES

The invention will be better understood in light of the following examples, which are given purely by way of illustration and the objective of which is not to limit the scope of the invention, defined by the appended claims.

Example 1: Deodorant Balm

A balm was prepared by mixing the ingredients in the weight proportions indicated below.

| | |
|---|---|
| Plant butters | 20.00% |
| Plant waxes and ester* | 9.00% |
| Plant oils | 24.00% |
| Glycerol | 6.00% |
| Sodium bicarbonate | 10.00% |
| Modified starch | 23.00% |
| Silica | 2.00% |
| Essential oils | qs |
| Antioxidant | qs |
| Fragrance | qs |
| Total: | 100.00% |

*including Acticire ® from GATTEFOSSE, containing polyglycerol-3 esters of C12-C30 fatty acids.

This balm may be packaged in pots and withdrawn using a spatula.

Example 2: Deodorant Balm

| | |
|---|---|
| Plant butters | 20.00% |
| Plant waxes and ester* | 9.00% |
| Plant oils | 33.00% |
| Glycerol | 6.00% |
| Sodium bicarbonate | 10.00% |
| Native starches | 20.00% |
| Antioxidant | 0.20% |
| Fragrance | 1.50% |

*including Acticire ® from GATTEFOSSE, containing polyglycerol-3 esters of C12-C30 fatty acids.

Example 3: Stability Test

Four samples A to D were taken from the composition of Example 1, which were divided up into four pillboxes stored respectively at 4° C., 25° C., 40° C. and 50° C. The stability of the samples A to C is evaluated every week for 1 month then every 15 days for 2 months and the stability of the sample D is evaluated every week for 1 month.

By way of comparison, the stability of a similar product was evaluated, this product containing: a plant butter, plant oils, glycerol, sodium bicarbonate, starch, essential oils and an antioxidant. This product contained no polyglycerol ester, wax or fatty-phase gelling agent. It was also divided up into four samples, as described above.

The appearance of the samples tested was observed. The results are presented in the table below:

| | Product tested | | | |
|---|---|---|---|---|
| | After 3 months at 4° C. | After 3 months at 25° C. | After 3 months at 40° C. | After 1 month at 50° C. |
| Example 1 | stable | stable | stable | stable |
| Comparative example | stable | stable | granular appearance; exudation starting from 1 week and darker color | phase separation starting from 1 week and browning |

It emerges from this test that the product according to the invention is more stable at 40° C., that is to say under accelerated aging conditions which are considered to be representative of the behavior of the product stored for three years under normal storage conditions.

Example 4: Sensory Analysis

A panel of 19 volunteers was recruited in order to evaluate the balm of Example 1. The product was applied under the armpits with the spatula, followed by a massage to make it penetrate into the skin.

The panelists predominantly considered that the product was easy to apply (17/19), limited the formation of perspiration odors (17/19) and provided good deodorant protection (16/19), without leaving marks on clothing (15/19).

Example 5: Sensory Analysis—Comparative Test

The balm of Example 2 was compared to a similar product containing: a plant butter, plant oils, glycerol, sodium bicarbonate, starch, essential oils and an antioxidant. This product contained no polyglycerol ester, wax or fatty-phase gelling agent.

In order to do this, 9 volunteers were recruited. On the morning of the test they were asked to wash their armpits with a neutral soap before applying, using a spatula, from 0.4 to 0.5 g of the balm of Example 2 under one armpit and the same amount of the comparative balm under the other armpit. The panelists were then clothed in a black Lycra T-shirt, prewashed using a neutral detergent, which they kept on for the whole day. The effectiveness of the balms was self-evaluated after 8 hours, in the test laboratory.

The balm of Example 2 was more effective than the comparative balm against perspiration odors after 8 h (no odor for 8 panelists as opposed to 6 panelists). Moreover it generated fewer marks on the T-shirt (no marks for 5 panelists as opposed to 3 panelists). Moreover, the panelists preferred the softer texture of the balm of Example 2.

The invention claimed is:

1. An anhydrous cosmetic composition containing:
   (a) from 5 to 15% by weight of at least one bicarbonate salt,
   (b) from 20% to 50% by weight of at least one oil,
   (c) at least one fatty-phase structuring agent,
   (d) glycerol, and
   (e) at least one polyglycerol ester of a fatty acid containing from 12 to 30 carbon atoms, said anhydrous composition containing less than 5%, by weight, of water, wherein the composition does not contain an aluminum salt.

2. The composition as claimed in claim 1, characterized in that the bicarbonate salt is present in an amount of 10% by weight, relative to the total weight of the composition.

3. The composition as claimed in claim 1, characterized in that the fatty-phase structuring agent is a least one ingredient selected from the group consisting of waxes of animal origin, waxes of plant origin, fatty-phase gelling agents and mixtures thereof, optionally combined with at least one plant butter.

4. The composition as claimed in claim 1, characterized in that the glycerol represents from 1% to 15% by weight relative to the total weight of the composition.

5. The composition as claimed in claim 1, characterized in that it additionally contains one or more pulverulent fillers in the form of porous or hollow microparticles.

6. The composition as claimed in claim 5, characterized in that the pulverulent fillers represent from 10% to 30% by weight, relative to the total weight of the composition.

7. A cosmetic process for treating human body odors comprising applying the composition as claimed in claim 1 to a human.

8. A deodorant product in the form of a tube, pot or any other packaging, in particular of oblong shape, suitable for dispensing a semi-solid composition, containing the composition as claimed in claim 1 in cream form.

9. A deodorant product in a packaging form suitable for dispensing a stick, containing the composition as claimed in claim 1 in stick form.

* * * * *